United States Patent
Yang et al.

(10) Patent No.: US 12,285,013 B2
(45) Date of Patent: Apr. 29, 2025

(54) **PROCESSING METHOD FOR INCREASING SEED PRODUCTION RATE OF SEED FRUITS OF *CUCUMIS SATIVUS L***

(71) Applicant: Yangzhou University, Yangzhou (CN)

(72) Inventors: Xiaodong Yang, Yangzhou (CN); Yizhuo Deng, Yangzhou (CN); Lili Zhang, Yangzhou (CN); Lei Qiu, Yangzhou (CN); Jieni Gu, Yangzhou (CN); Xuehao Chen, Yangzhou (CN)

(73) Assignee: Yangzhou University, Yangzhou (CN)

( * ) Notice: Subject to any disclaimer, the term of this patent is extended or adjusted under 35 U.S.C. 154(b) by 0 days.

(21) Appl. No.: 18/816,245

(22) Filed: Aug. 27, 2024

(65) Prior Publication Data

US 2024/0415122 A1  Dec. 19, 2024

(30) Foreign Application Priority Data

Sep. 13, 2023 (CN) .......................... 202311174307.9

(51) Int. Cl.
*A01N 43/66* (2006.01)
*A01H 3/04* (2006.01)
*A01N 25/30* (2006.01)
*A01P 21/00* (2006.01)

(52) U.S. Cl.
CPC ................ *A01N 43/66* (2013.01); *A01H 3/04* (2013.01); *A01N 25/30* (2013.01); *A01P 21/00* (2021.08)

(58) Field of Classification Search
CPC .......... A01G 22/05; A01N 43/66; A01P 21/00
See application file for complete search history.

(56) References Cited

FOREIGN PATENT DOCUMENTS

CN    113711867 A    11/2021

OTHER PUBLICATIONS

Huimin Zhang, "Research on the Relationship between Polyadenylation and DNA Methylation Regulation in Cucumber (*Cucumis sativus* L.) Source-Sink Relationship", Full-text Database of Excellent Chinese Master's Theses (Electronic Journal), Issue 1, 2023, Jan. 15, 2023, pp. D048-D173.
CNIPA, Notification of First Office Action for Chinese application CN202311174307.9, Mar. 23, 2024.
CNIPA, Notification to grant patent right for Chinese application CN202311174307.9, May 20, 2024.

*Primary Examiner* — Susan McCormick Ewoldt
(74) *Attorney, Agent, or Firm* — Hemisphere Law, PLLC; Zhigang Ma

(57) ABSTRACT

The present invention relates to a processing method for increasing seed production rate of seed fruits of *Cucumis sativus* L., comprising the following steps: (1) preparing a plant growth regulator according to a formula proportion; (2) selecting seed fruits of *Cucumis sativus* L. growing naturally in a greenhouse and reaching a pollination stage, and dipping female flowers thereof with the plant growth regulator prepared in step (1) before pollination; (3) picking male flowers for pollination after the female flowers are completely dry; (4) dipping the pollinated female flowers again; (5) conducting field routine cultivation management. The present invention uses a DNA methyltransferase inhibitor "5-azacytidine" ($C_8H_{12}N_4O_5$) to treat the seed fruits of *Cucumis sativus* L. by soaking and dipping, wherein 5-azacytidine increases seed production efficiency by reducing fruit length of the seed fruits, reducing fruit weight and reducing nutrient loss for fruit growth.

6 Claims, 6 Drawing Sheets

PROCESSING METHOD FOR INCREASING SEED PRODUCTION RATE OF SEED FRUITS OF *CUCUMIS SATIVUS L*

TECHNICAL FIELD

The present invention relates to a processing method for increasing seed production rate of seed fruits of *Cucumis sativus* L., and belongs to the technical field of vegetable seed production.

BACKGROUND

*Cucumis sativus* L. is a common vegetable that belongs to the family of cucurbitaceae plants. *Cucumis sativus* L. is widely cultivated all over the world, among which China has the widest cultivation area and the highest yield. *Cucumis sativus* L. is loved by people for the freshness, diverse eating ways and high nutritional value thereof, and demand for *Cucumis sativus* L. is growing year by year. Therefore, it is of great significance to explore and increase seed production efficiency of seed fruits of *Cucumis sativus* L. in order to achieve high-yield cultivation technology of *Cucumis sativus* L.

In an appropriate range, elongation and weight gain of *Cucumis sativus* L. are positively correlated with chemical fertilizer application amount. For the seed fruits of *Cucumis sativus* L., fertilizer cost can be saved and more nutrients can be supplied to seeds by reducing fruit length and reducing fruit weight without affecting the number and quality of the seeds, so as to achieve the purpose of increasing the seed production efficiency.

At present, methods for increasing seed production efficiency of seed fruits of *Cucumis sativus* L. are relatively simple, most of which are to optimize field management; the steps are more complicated and the cycle is long, and the methods are time-consuming and laborious.

SUMMARY

The purpose of the present invention is to provide a processing method for increasing seed production rate of seed fruits of *Cucumis sativus* L. in view of the above problems in the prior art on the basis of the prior art from a different perspective, which is a processing method for increasing seed production efficiency of seed fruits of *Cucumis sativus* L. by reducing fruit length and reducing fruit weight of *Cucumis sativus* L.; the method has low cost and simple operation, and can be applied simultaneously with the prior art, so that the seed production efficiency of the seed fruits can be increased more significantly.

To achieve the above invention purpose, the present invention adopts the following technical solution:

An application of 5-azacytidine ($C_8H_{12}N_4O_5$) in preparing a plant growth regulator for increasing seed production efficiency of seed fruits of *Cucumis sativus* L.

A plant growth regulator, prepared by mixing a 5-azacytidine solution and an emulsifier Tween 80, wherein the 5-azacytidine solution has a concentration of 50 μM, and proportion of the 5-azacytidine solution to the emulsifier Tween 80 is 10000:1.

A processing method for increasing seed production efficiency of seed fruits of *Cucumis sativus* L., comprising the following steps:

(1) Preparing a plant growth regulator according to a formula proportion;

Preparing a 5-azacytidine solution with a concentration of 50 μM, adding an emulsifier Tween 80 at the same time, and mixing the 5-azacytidine solution and the emulsifier Tween 80 at a proportion of 10000:1 to obtain the plant growth regulator;

(2) Selecting seed fruits of *Cucumis sativus* L. growing naturally in a greenhouse and reaching a pollination stage, and dipping female flowers thereof with the plant growth regulator prepared in step (1) before pollination;

(3) Picking male flowers for pollination after the female flowers are completely dry;

(4) Dipping the pollinated female flowers again;

(5) Conducting field routine cultivation management.

In step (1), the prepared plant growth regulator is preserved in a refrigerator at 4° C.

In step (2), the preserved solution of the prepared plant growth regulator is poured into any container, and the female flowers of the seed fruits of *Cucumis sativus* L. reaching a pollination stage are completely immersed in the plant growth regulator in the container for at least 5 seconds.

In step (2), in the greenhouse, the temperature is stabilized at 20° C.-35° C., the humidity is 70%-90%, the pH value of the cultivation soil is 6.5, a selected species of *Cucumis sativus* L. is a species of North China *Cucumis sativus* L. used for seed production, a row spacing for seed fruit cultivation is fixed at 75 cm, a planting distance is 25 cm, and the number of plants planted in each row is 80.

Step (3) is specifically as follows: picking male flowers blooming on the same plant, removing all petals, poking stamens of the male flowers into the female flowers after the female flowers soaked and dipped by the plant growth regulator are completely dry, and repeating the process for multiple times to increase pollination success rate.

Step (4) is specifically as follows: repeating the soaking and dipping treatment described in step (2) for successfully pollinated female flowers of *Cucumis sativus* L. on the third day after pollination.

The method of the present invention is advanced and scientific. In a first aspect of the present invention, an application of a DNA methyltransferase inhibitor "5-azacytidine" as a reagent for increasing seed production efficiency of seed fruits of *Cucumis sativus* L. is provided. In a second aspect of the present invention, a plant growth regulator is provided. The present invention uses the DNA methyltransferase inhibitor "5-azacytidine" to treat the female flowers of *Cucumis sativus* L. in the pollination stage, which can significantly reduce the fruit length of *Cucumis sativus* L. and significantly reduce the weight of *Cucumis sativus* L. without affecting the number of seeds, so that the seed production efficiency of the seed fruits of *Cucumis sativus* L. is increased, and a new method for high-yield cultivation of *Cucumis sativus* L. is provided.

In a third aspect of the present invention, a processing method for increasing seed production efficiency of seed fruits of *Cucumis sativus* L. is provided, which mainly comprises the following steps:

(1) Preparing a reagent. Specifically: preparing a 5-azacytidine solution with a concentration of 50 μM, adding an emulsifier Tween 80 at the same time according to a proportion of 10000:1, and preserving the reagent in a refrigerator at 4° C.

(2) Selecting seed fruits of *Cucumis sativus* L. growing naturally in a greenhouse and reaching a pollination stage, and dipping female flowers thereof with the reagent prepared in step (1) before pollination. Specifically: pouring the prepared and preserved solution into any container, and completely immersing the female flowers of the seed fruits of *Cucumis sativus* L. reaching a pollination stage in the reagent for at least 5 seconds.

(3) Pollinating the female flowers of *Cucumis sativus* L. Specifically: picking male flowers blooming on the same plant, removing all petals, poking stamens of the male flowers into the female flowers after the female flowers soaked and dipped by the reagent are completely dry, and repeating the process for multiple times to increase pollination success rate.

(4) Dipping the pollinated female flowers again. Specifically: repeating the soaking and dipping treatment described in step (2) for successfully pollinated female flowers of *Cucumis sativus* L. on the third day after pollination.

(5) Conducting field cultivation management normally.

In the present invention, by soaking and dipping with 5-azacytidine during the pollination stage of the seed fruits of *Cucumis sativus* L., the fruit length of the seed fruits is significantly reduced and the seed production efficiency of the seed fruits of *Cucumis sativus* L. is increased without affecting the number of seeds of the seed fruits; in addition, the present invention has simple operation and low cost, and can be applied simultaneously with the prior art.

To sum up, the present invention uses the DNA methyltransferase inhibitor "5-azacytidine" ($C_8H_{12}N_4O_5$) to treat the seed fruits of *Cucumis sativus* L. by soaking and dipping, wherein 5-azacytidine increases the seed production efficiency by reducing fruit length of the seed fruits, reducing fruit weight and reducing nutrient loss for fruit growth. Based on the study of fruit length and weight phenotype of *Cucumis sativus* L., the method of the present invention can increase the seed production efficiency of the seed fruits of *Cucumis sativus* L. and provide support for high-yield cultivation technology of *Cucumis sativus* L.

DETAILED DESCRIPTION

Figure 1:
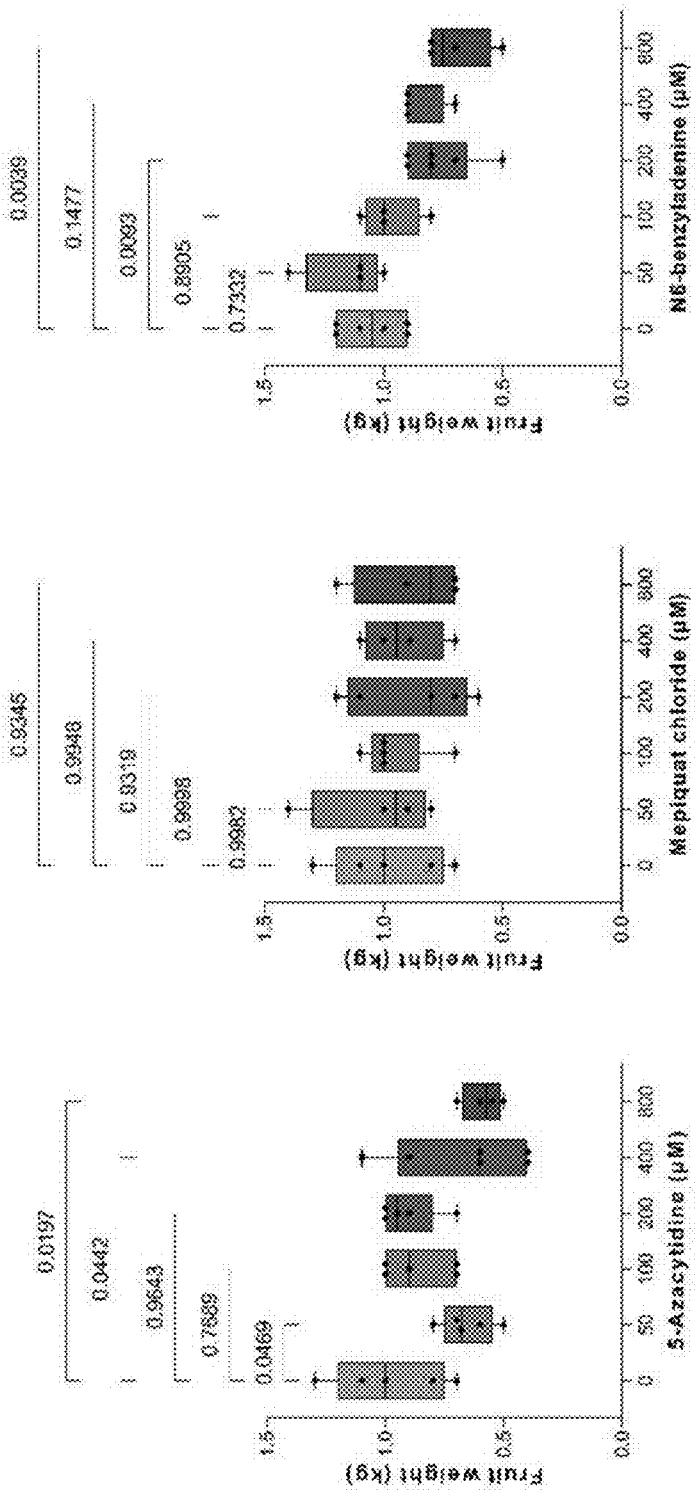
FIG. 1 shows statistics of fruit length of seed fruits of *Cucumis sativus* L. after soaking and dipping with 5-azacytidine, mepiquat chloride and N6-benzyladenine with different concentrations.
Figure 2:
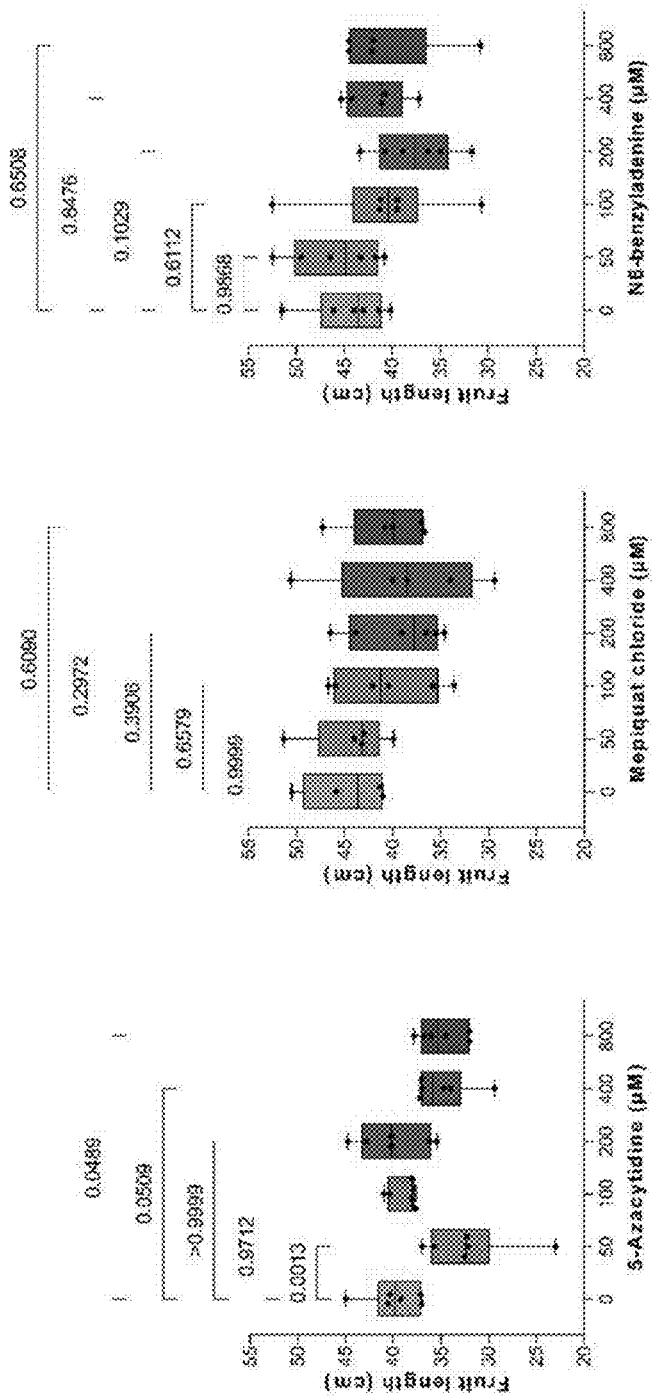
FIG. 2 shows statistics of weight of seed fruits of *Cucumis sativus* L. after soaking and dipping with 5-azacytidine, mepiquat chloride and N6-benzyladenine with different concentrations.
Figure 3:
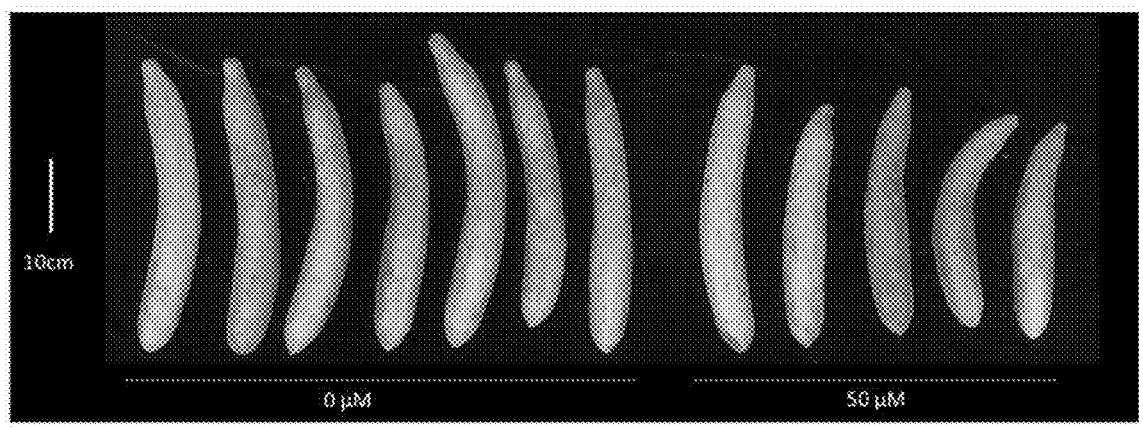
FIG. 3 shows phenotype of seed fruits of *Cucumis Sativus* L. after soaking and dipping with 5-azacytidine with a concentration of 0 µM (left) and phenotype of seed fruits of *Cucumis Sativus* L. after soaking and dipping with 5-azacytidine with a concentration of 50 µM (right)
Figure 4:
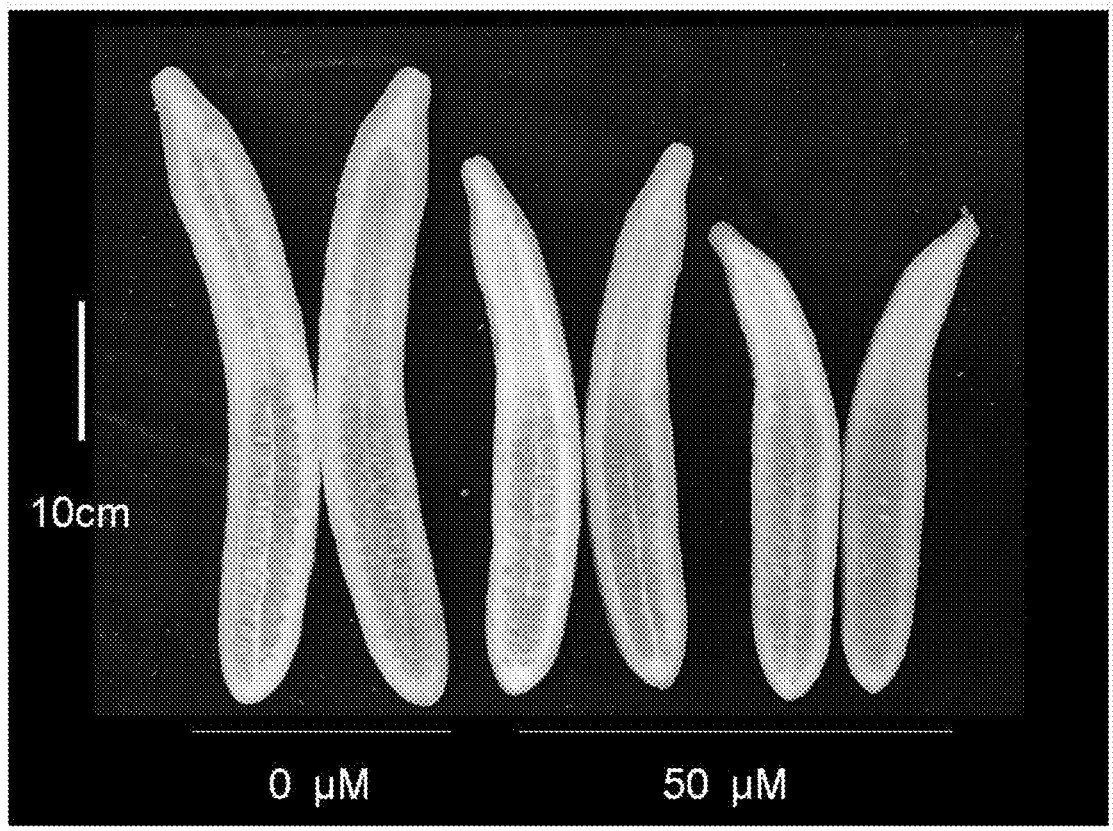
FIG. 4 shows phenotype for cross sections of seed fruits of *Cucumis Sativus* L. after soaking and dipping with 5-azacytidine with a concentration of 0 µM (left) and phenotype for cross sections of seed fruits of *Cucumis Sativus* L. after soaking and dipping with 5-azacytidine with a concentration of 50 µM (right)
Figure 5:
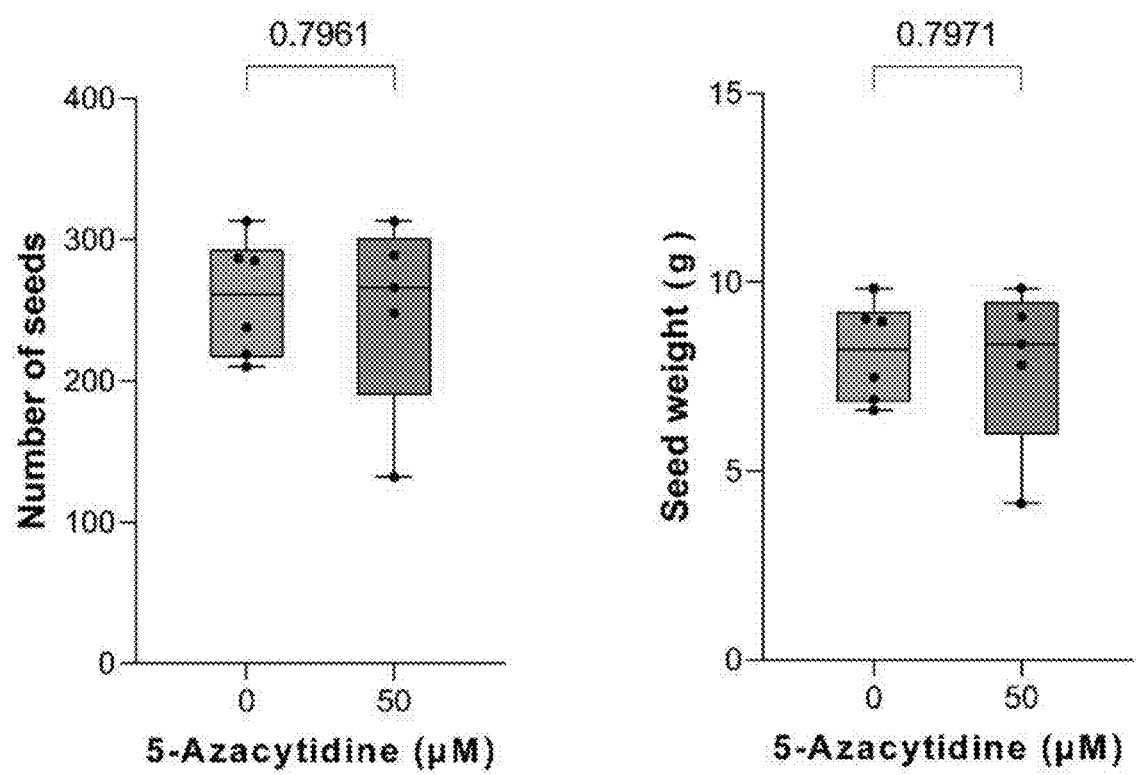
FIG. 5 shows statistics of number of seeds and seed weight of seed fruits of *Cucumis sativus* L. after soaking and dipping with 5-azacytidine with a concentration of 50 µM.
Figure 6:
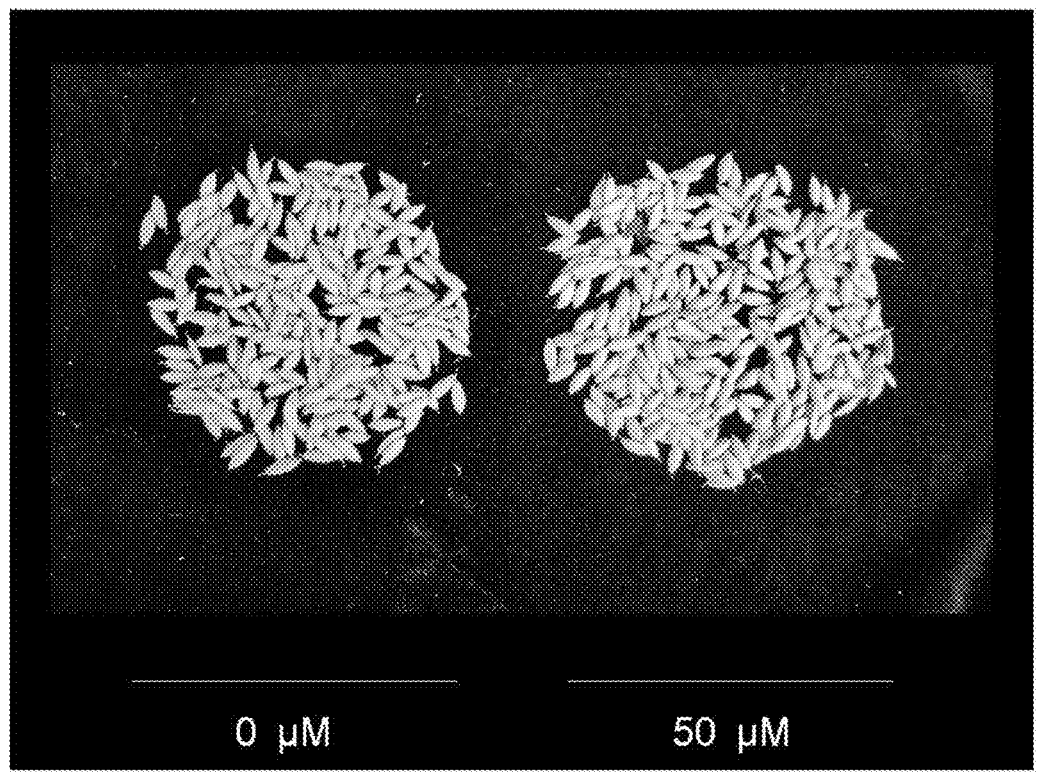
FIG. 6 shows phenotype for seeds of seed fruits of *Cucumis Sativus* L. after soaking and dipping with 5-azacytidine with a concentration of 0 µM (left) and phenotype for seeds of seed fruits of *Cucumis Sativus* L. after soaking and dipping with 5-azacytidine with a concentration of 50 µM (right).

The present invention will be further described below in combination with the detailed description, and the detailed description is not the basis of limitation to the present invention.

A processing method for increasing seed production efficiency of seed fruits of *Cucumis sativus* L., comprising the following steps:

(1) Preparing a 5-azacytidine solution with a concentration of 50 µM, adding an emulsifier Tween 80 at the same time according to a proportion of 10000:1 to obtain a plant growth regulator, and preserving the prepared plant growth regulator in a refrigerator at 4° C.

(2) Pouring the prepared and preserved plant growth regulator into any container, selecting seed fruits of *Cucumis sativus* L. growing naturally in a greenhouse and reaching a pollination stage, and completely immersing female flowers thereof in the reagent before pollination for at least 5 seconds.

(3) Picking male flowers blooming on the same plant, removing all petals, poking stamens of the male flowers into the female flowers after the female flowers soaked and dipped by the plant growth regulator are completely dry, and repeating the process for multiple times to increase pollination success rate.

(4) Repeating the same soaking and dipping treatment for successfully pollinated female flowers of *Cucumis sativus* L. on the third day after pollination.

(5) Conducting field cultivation management normally.

In step (2), in the greenhouse, the temperature is stabilized at 20° C.-35° C., the humidity is 70%-90%, the pH value of the cultivation soil is 6.5, a selected species of *Cucumis sativus* L. is a species of North China *Cucumis sativus* L. used for seed production, a row spacing for seed fruit cultivation is fixed at 75 cm, a planting distance is 25 cm, and the number of plants planted in each row is 80.

The above detailed description only describes specific embodiments of the present invention, but the technical features of the present invention is not limited thereto. Other embodiments derived by those skilled in the art without deviating from the technical solution of the present invention shall be covered within the patent scope of the present invention.

The invention claimed is:

1. A method of preparing and applying an application of 5-azacytidine ($C_8H_{12}N_4O_5$) in increasing seed production efficiency of seed fruits of *Cucumis sativus* L., comprising a processing method for increasing seed production efficiency of seed fruits of *Cucumis sativus* L., wherein the method comprises the following steps:

(1) preparing a plant growth regulator according to a formula proportion;
preparing a 5-azacytidine solution with a concentration of 50 µM, adding an emulsifier Tween 80 at the same time, and mixing the 5-azacytidine solution and the emulsifier Tween 80 at a proportion of 10000:1 to obtain the plant growth regulator;

(2) selecting seed fruits of *Cucumis sativus* L. growing in a greenhouse and reaching a pollination stage, and dipping female flowers thereof with the plant growth regulator prepared in step (1) before pollination;

(3) picking male flowers for pollination after the female flowers are completely dry;

(4) dipping the pollinated female flowers again.

2. The method according to claim 1, wherein in step (1), the prepared plant growth regulator is optionally preserved in a refrigerator at 4° C.

3. The method according to claim 1, wherein in step (2), the female flowers of the seed fruits of *Cucumis sativus* L. reaching a pollination stage are completely immersed in the plant growth regulator for at least 5 seconds.

4. The method according to claim 1, wherein in step (2), in the greenhouse, the temperature is 20° C.-35° C., the humidity is 70%-90%, the pH value of the cultivation soil is 6.5, a selected species of *Cucumis sativus* L. is a cultivated variety from North China used for seed production, a row spacing for seed fruit cultivation is fixed at 75 cm, a planting distance is 25 cm, and the number of plants planted in each row is 80.

5. The method according to claim 1, wherein step (3) is specifically as follows: picking male flowers blooming on the same plant, removing all petals, poking stamens of the male flowers into the female flowers after the female flowers soaked and dipped by the plant growth regulator are completely dry, and repeating the process for multiple times to increase pollination success rate.

6. The method according to claim 1, wherein step (4) is specifically as follows: repeating the soaking and dipping treatment described in step (2) for successfully pollinated female flowers of *Cucumis sativus* L. on the third day after pollination.

* * * * *